United States Patent [19]

Feinbloom

[11] Patent Number: 4,621,283
[45] Date of Patent: Nov. 4, 1986

[54] HEAD-MOUNTED COAXIAL IMAGE SYSTEM FOR SURGEONS

[75] Inventor: Richard E. Feinbloom, New York, N.Y.

[73] Assignee: Designs For Vision, Inc., Ronkomkoma, N.Y.

[21] Appl. No.: 644,852

[22] Filed: Aug. 27, 1984

[51] Int. Cl.$^4$ ............ A61B 1/04; A61B 1/06; F21V 13/06
[52] U.S. Cl. .................. 358/93; 128/22; 362/33; D26/39
[58] Field of Search ............ 358/93, 108; 128/22; 362/33; D26/39

[56] References Cited

U.S. PATENT DOCUMENTS

| | | | |
|---|---|---|---|
| D. 266,192 | 9/1982 | Feinbloom | D26/39 |
| 2,539,104 | 1/1951 | Rodel | 128/22 |
| 2,990,765 | 7/1961 | Winzenburg | 128/6 |
| 3,589,799 | 6/1971 | Hotchkiss | 128/22 |
| 3,959,612 | 5/1976 | Feinbloom | 362/33 |
| 4,102,333 | 7/1978 | Storz | 128/22 |
| 4,364,645 | 12/1982 | Feinbloom | 351/120 |
| 4,395,731 | 7/1983 | Schoolman | 128/4 |
| 4,544,953 | 10/1985 | Goldman | 358/227 |

Primary Examiner—Howard W. Britton
Attorney, Agent, or Firm—Arthur L. Plevy

[57] ABSTRACT

There is disclosed a head-mounted imaging system which system employs a headband to be worn on the head of a surgeon during a surgical procedure. A surgeon may utilize a microscope eyeglass assembly in order for him to achieve a desired magnification of the operating area. The headband assembly includes an imaging system which imaging system furnishes a beam of light which beam of light is reflected into the operating area by means of a tiltable mirror coupled to the headband assembly. The tiltable mirror receives the reflected image from the operating site. This image is received by the imaging system where it is directed through a zoom lens magnification assembly whereby the magnification of the lens assembly is set to correspond to the microscope eyeglass assembly worn by the surgeon. The image thus directed through the zoom lens assembly is then coupled to a television monitor pickup for eventual viewing on a television monitor to thereby enable observers to view the entire operation as if through the eyes of the surgeon.

20 Claims, 2 Drawing Figures

HEAD-MOUNTED COAXIAL IMAGE SYSTEM FOR SURGEONS

BACKGROUND OF THE INVENTION

This invention relates to an imaging system for medical purposes and more particularly for a head-mounted imaging system employing a microscope assembly coupled to a television monitor which assembly operates in conjunction with a microscope eyeglass assembly worn by the surgeon during an operation.

Utilizing present techniques, it is well known that the surgical procedures which are employed in the operating room during an operation can only be viewed by others to a limited extend. Essentially, a skilled surgeon, while performing an operation, would like to teach the techniques to his students and associates, and hence there are many people in the operating room who would like to view the operation. It is, of course, understood that in regard to this there have been many approaches including photography, television and so on employed by the prior art.

Essentially, all such approaches of the prior art required a separate camera which was focussed on the area of the patient where the operation was being performed. In regard to such procedures it is understood that while the onlookers could view the procedure, they did not see the operating site in the same manner and from the same view as the surgeon. This is an important aspect in regard to the teaching process where it is desirable that the student or the assistant view the operation and the procedure in the same manner as the surgeon.

The prior art being cognizant of such problems has developed various devices which attempt to solve the problem and which are cognizant of the problem. For example see U.S. Pat. No. 2,990,765 entitled STEREO CAMERA FOR SCIENTIFIC AND SURGICAL PHOTOGRAPHS issued on July 4, 1961 to W. Winzenberg. This patent discloses a head-mounted camera which is secured to the forehead of an operator and out of his line of vision. The structure includes light projection means which are connected to a camera for indicating picture area limits by casting patterns of light into the work area. The main objective of the patent is to allow the surgeon to continue with the operating procedure while further being able to take pictures without moving his head.

Other patents such as U.S. Pat. No. 4,102,333 entitled HEAD MOUNTED LAMP WITH JOINT OBERSERVATIONS EYEPIECE issued on July 25, 1978 to K. Storz. This patent shows a concave mirror mounted on the headband. A support for the mirror has a viewing path on which is incorporated a prism to allow a second person to observe what the surgeon observes by looking through the viewing tube. Essentially, this structure is relatively complicated and unwieldy and has not been widely accepted in such procedures. A major problem which has not been solved by the prior art is the fact that many surgeons such as those engaged in the field of neurosurgery employ microscope eyeglass assemblies during an operation procedure. These assemblies essentially poovide a definite magnification for the eyes of the surgeon which allows him to view the operating area with magnification such as 2.5× to 8.0× or greater. Hence in such a system the surgeon is actually viewing the operation sight in magnified mode. It is, of course, understood that the onlooker or that person who is attempting to observe the procedure should also view the entire procedure at the same magnification as the surgeon. Coupled with this is the necessity for providing the viewer with a representation of the operating area as seen from the eyes of the surgeon. Hence the imaging system employed in this invention provides a coaxial image for eventual display on a video monitor and for presentation to an auxiliary display device such as a television monitor.

It is a further object of the present invention to provide a head-mounted illumination system which system is extremely light weight, easy to use and is compatible with the magnification afforded by a microscope eyeglass assembly employed by a surgeon during an operation.

BRIEF DESCRIPTION OF THE PREFERRED EMBODIMENT

A head-mounted coaxial imaging system of the type adapted to be supported on the head of the user by means of a headband worn by the user comprising a tiltable reflecting surface mounted on said headband and positioned above the eyes of said user when said headband is being worn, a housing coupled to said headband and positioned above the head of said user said housing having an internal hollow and a front portion extending from said headband and overlying said reflecting surface, light means associated with said housing to project a beam of light with said beam directed to the surface of said reflecting surface whereby said beam as reflected is directed toward an area of observation, an adjustable magnification means located in the hollow of said housing and operative to receive an image of said area of observation as reflected by said tiltable reflecting surface for magnifying said image of said area according to the preferences of said viewer and means optically coupled to said magnification means for producing a viewable image of said area of observation.

DETAILED DESCRIPTION OF THE FIGURES

Figure 1:
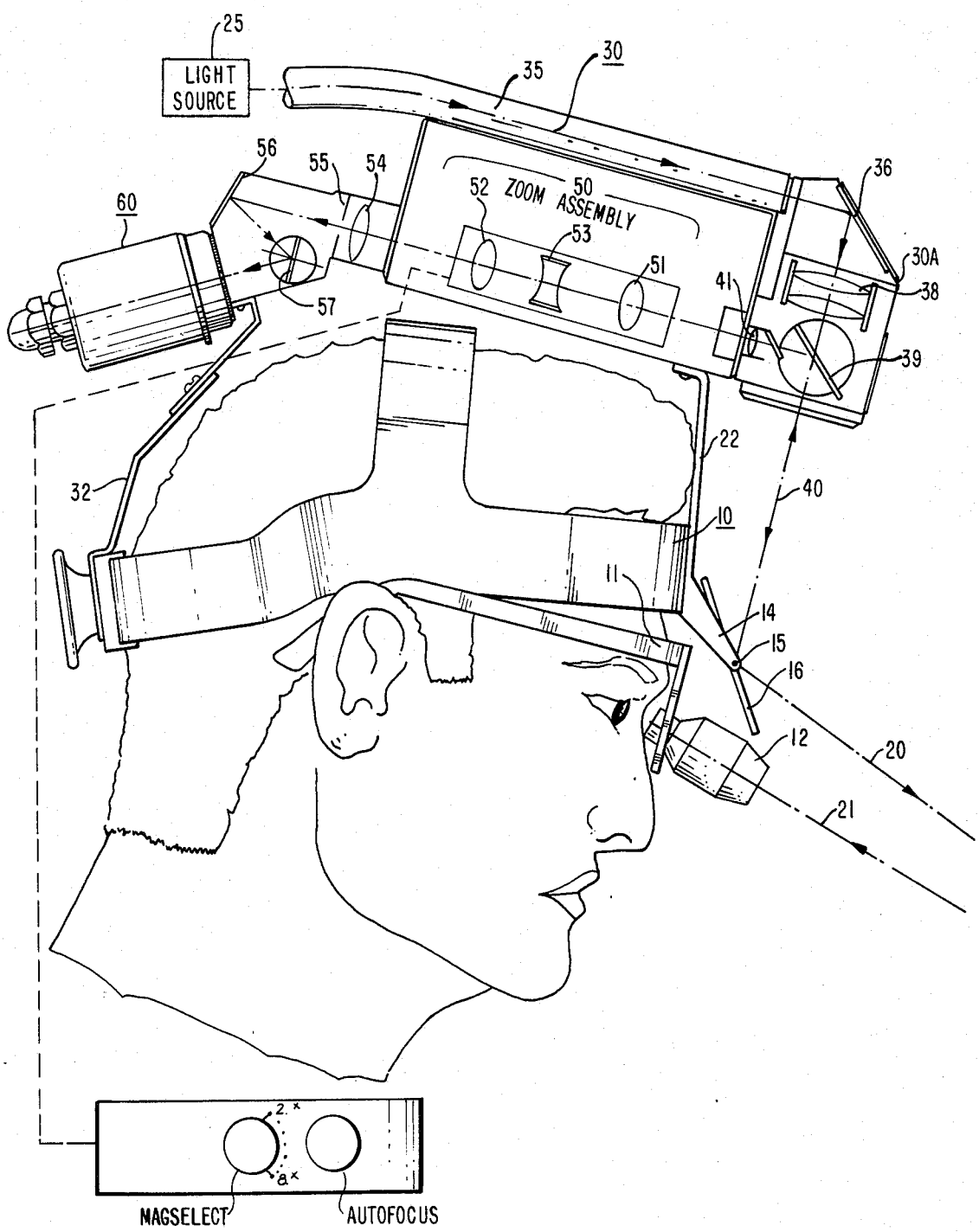
FIG. 1 is an enlarged side-elevation view of a head-mounted optical image system according to this invention.

Referring to FIG. 1, there is shown a representation of a head of a surgeon who is shown in the figure is wearing a headband assembly 10.

Headbands are well known and have been employed by surgeons for many years. Such devices as headband 10 are completely adjustable and can be adjusted to accommodate the head of any individual. For an example of a typical headband assembly, reference is made to U.S. Pat. No. Des. 266,192 entitled SURGICAL HEADLIGHT OR SIMILAR ARTICLE issued on Sept. 14, 1984 to R. E. Feinbloom and assigned to Designs for Vision, Inc., the assignee herein. As will be explained, the headband 10 has coupled thereto an imaging system which essentially includes an automatically adjustable lens assembly which is utilized to provide a magnification to the image viewed by the surgeon and also includes a television monitor pickup which produces a television signal for application to a video monitor.

As indicated above, the surgeon normally wears a microscope eyeglass assembly 11 which assembly includes a typical eyeglass frame having directed from each eyepiece a magnifying lens assembly contained in a separate housing as 12. For example of such structures reference is made to U.S. Pat. No. 4,364,645 entitled ADJUSTABLE FRAME APPARATUS FOR TELESCOPIC SPECTACLES issued on Dec. 21, 1982 and assigned to the assignee herein. The microscope eyeglass assembly as indicated, affords magnification to the eyes of the surgeon and which magnification can vary according to the requirements of the surgeon from 2.5× to 8.0× or greater. In this manner, when the surgeon is performing critical procedures such as in the field of neurosurgery, he experiences a magnified view of the area of the observation.

As seen in the figure, the headband 10 contains a front bracket 14 which is downwardly oriented from the front of the headband. The bracket 14 is a U-shaped bracket having a left and right pivot point 15 to accommodate a tiltable mirror assembly 16. The mirror assembly 16 has a flat reflecting surface and essentially receives an image from the site of the operating area and designated by the line 20. The image received by the mirror 16 is essentially coaxial with the image or the line of sight 21 as viewed by the surgeon. As seen in the figure, a further bracket 22 is coupled to the headband 10 and supports an image system 30 at the front of the headband while a second adjustable bracket 32 supports the imaging assembly 30 at the rear of the headband.

Apart from the magnification required by the surgeon during an operating procedure, the surgeon will also desire that the area upon which he is operating is illuminated for a clearer view. Illumination of this area should be automatic, and hence, as the surgeon moves his head, the beam of light which impinges upon the area should move accordingly. Thus as shown in FIG. 1, the imaging system 30 supports a fiber optic cable 35. The cable 35 is directed to a cold light source 25 which essentially is an operating room light assembly for producing a high intensity beam of light which beam of light is coupled to the optical cable 35. For an example of a typical light source including a fiber optic cable coupled thereto, reference is made to U.S. Pat. No. 3,959,612 entitled ROTARY SWITCH ASSEMBLY PARTICULARLY ADAPTED FOR USE WITH FIBER OPTIC LIGHT SOURCES issued on May 25, 1976 to R. R. Feinbloom and assigned to the assignee herein.

Thus the fiber optic cable 35 propagates a beam of light which beam of light impinges upon the reflecting surface of a mirror 36 which is essentially positioned on the inner surface of a first housing section 30a forming part of the housing for the imaging system 30. As seen from the figure, the reflecting mirror 36 has a flat reflecting surface and essentially is a first surface mirror having maximum reflection.

The mirror is positioned on the inner wall of the housing 30a at an angle of about 45 degrees. The light beam emanating from the mirror is then directed through a condensing lens assembly 38 to produce a concentrated beam which beam is directed through a semi-transparent mirror 39 to impinge upon the surface of the tiltable mirror 16 as coupled to the headband assembly 10. In this manner, the beam of light 40 is directed in a coaxial manner from the housing 30a to the viewing area via the optical path 20. The optical path 20 also carries the image of the viewing area back to the optical assembly.

As seen in FIG. 1, the mirror 39 which is again positioned at a 45 degree angle receives the image of the viewing area and directs the image through an objective lens assembly 41. This image is then directed through a zoom lens assembly 50. Essentially, as will be further explained, the zoom lens assembly 50 consists of an upper lens 51 and a lower lens 52. Positioned between lenses 51 and 52 is a magnification lens assembly 53. The zoom lens assembly, as will be explained, produces a magnification for the image which magnification is compatible with the magnification afforded the surgeon via the microscope eyeglass assembly 11. The magnified image emanating from lens 52 is then directed to an objective lens assembly 54. The objective lens assembly 54 is associated with a variable iris which iris controls the diameter of the image as received from the objective lens assembly 54. The light image emanating from iris 55 is directed to the surface of an adjustable mirror 56 where it is further directed to a second ajustable mirror 57. Essentially the mirrors 56 and 57 serve to realign the image to present it to a television monitor pickup 60 which is mounted on the imaging assembly.

The television monitor pickup is an extremely small assembly and, essentially, is a CCD television camera (charged coupled device) which is a commercially available unit. Such units are extremely light and small. An example of a suitable commercial unit is manufactured by M-P Video Inc. located in Massachusetts and essentially is a miniature television camera assembly.

The output from the unit 60 is then directed to video monitor where the image is displayed for view. As can be seen from the above, the entire head band assembly which includes the imaging system 30 functions to illuminate the operating area site by means of the beam of light furnished by the fiber optic cable 35. The beam of light is directed upon the surface of the tiltable mirror 16 where the image from the site is also directed along the same line and is then propagated to the zoom lens assembly for transmission to the television monitor pickup 60. In this manner the line of sight of the surgeon and the optical image from the viewing site are coaxial. As one can ascertain, the surgeon, by means of the microscope eyeglass assembly 11, defines the working depth for the entire optical system and, by moving his head, automatically, illuminates the operating area by pointing the headlight according to head movement. Thus the image which is returned from the operating site is always directed along the same line as the illumination pattern.

As one can ascertain, the surgeon does not in any manner have to touch or adjust the apparatus once it is accommodated on his head. The working distance of a surgeon varies according to his preference and can be accurately adjusted to be accommodated by the microscope eyeglass assembly 11. This working distance once defined by the surgeon remains constant as this is the distance that the surgeon is best able to clearly view the operation. Typical distances are between 10 to 20 inches. Essentially, as one can ascertain, the video image which is produced by the television monitor pickup enables those viewing the monitor to see exactly what the surgeon sees.

The surgeon, by moving his head, automatically aims the headlight, and the eyes of the surgeon perceives the area illuminated by the beam which then, based on the orientation of the optical system, produces an image which essentially is completely indicative of exactly what the surgeon is seeing and, as will be explained, at the same magnification. The zoom lens assembly 50 which is accommodated in the imaging system housing is associated with a magnification selection mode which, therefore, enables the surgeon to set the magnification of the zoom lens in accordance with the magnification afforded by the microscope eyeglass assembly 11. The zoom lens assembly also is automatically focussed so that maximum focussing resolution is provided by the system on an automatic basis.

Figure 2:
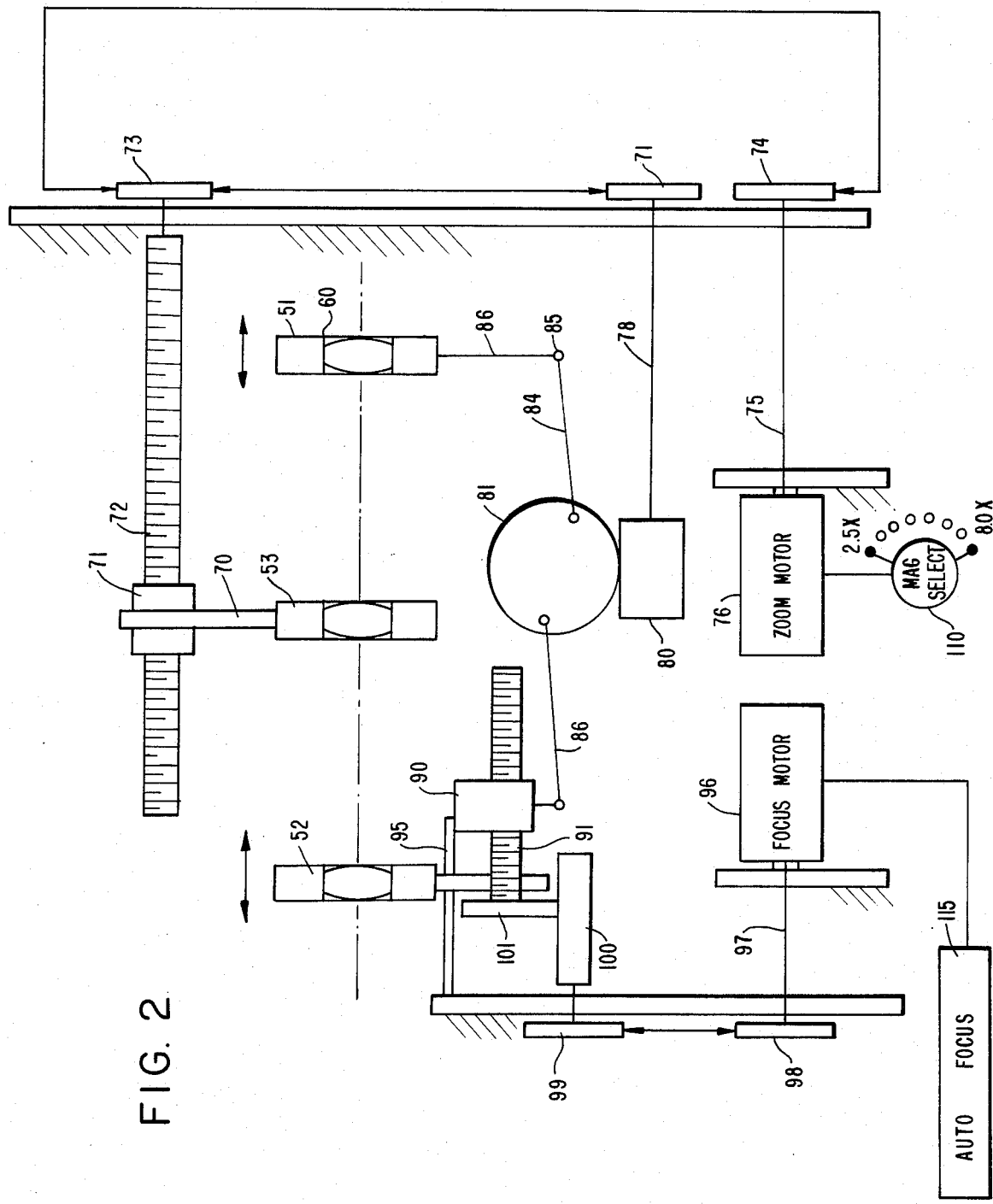
FIG. 2 is a schematic assembly of a zoom lens magnification system utilized with this invention.

Referring to FIG. 2, there is shown a mechanical schematic diagram indicating the operation of the zoom lens assembly 50 as depicated in FIG. 1 and as included in the housing 30. As indicated in FIG. 1, the optical assembly consists of an upper lens assembly 51 which is a doublet consisting of a combination of a convex and a concave lens assembly. The lens assembly 51 is contained in a lens holder 60. The lower lens assembly 52 is shown in the schematic with the magnification lens assembly 53 disposed between the upper lens assembly 51 and the lower lens assembly 52.

As indicated, the lens assembly provides magnification control whereby the distance between the lenses, as for example, the distance from lens 52 to lens 53 and the distance from lens 53 to lens 51 determines the magnification afforded by the system. This is conventional optics. The focussing of the lens assembly is also a function of the spacing of the lenses, and as will be explained, magnification and focussing are individually controlled. The lens 53 which is the magnification lens is preferably a symmetrical triplet lens assembly while both the upper and lower lens assemblies 51 and 52 are doublets. The magnification lens assembly 53 is secured by means of a rod 70 to a movable nut 71 which rides on a rotatable screw threaded member 72. The member 72 is coupled to a gear 73 which is driven by a gear 74 and denoted on the drawings by means of the coupling arrow indications. The gear 74 has the central point coupled via shaft 75 to a motor assembly 76 which is a DC motor.

The gear 73 is also coupled to another gear 77 which has a shaft 78 coupled to a worm member 80 which is a single threaded worm and which worm assembly 80 engages peripheral teeth or the periphery of a drive wheel 81. The drive wheel 81 has a segmented arm assembly 84 which has an articulated pivot 85 where an upper arm 86 emanating from the articulated pivot 85 is coupled to the housing 60 associated with the upper lens 51.

Located on the opposite side of the wheel 81 is another articulated arm assembly 86 of a different length from the assembly 84 which assembly is coupled to a movable nut 90 which rides on a threaded screw 91. The upper lens assembly 52 is coupled to the screw 91 and also is constrained to move along the rod 95 so that the lens assembly 52 can move in the direction of the arrow shown, as will be explained.

There is a separate focussing motor 96 which has a shaft 97 coupled to a gear 98 which gear drives another gear 99 having a shaft coupled to a pinion 100 which pinion drives gear 101 associated with the threaded screw 91 upon which the nut 90 rides. As can be seen from FIG. 2, the zoom lens assembly 50 enables the surgeon to set or control the zoom motor 76 so that the magnification afforded by the assembly can be selected by means of a suitable selection knob 110 labled Mag Select. The switch 110 consists of a plurality of positions to enable the surgeon to set or adjust the magnification of the lens assembly according to the magnification of his microscope eyeglass assembly and, for example, from 2.5× to 8.0× in increments of 0.5.

As one can see from FIG. 2, upon moving the selector switch 110 to the appropriate position, one now activates motor 76 which in turn causes the gears 73, 74 and 77 to rotate. This in turn changes the position between the lens assemblies 51, 52, and 53 to thereby afford a different magnification for each setting of switch 110. The focus motor 96 is controlled by an electronic circuit 115 designated as auto-focus.

Focussing techniques for automatically focussing an optical image are well known. In particular circuit 115 contains automatic focussing circuitry which is fully described in a co-pending application entitled VIDEO AUTOMATIC FOCUSSING SYSTEM, Ser. No. 479,457, filed on Mar. 28, 1983 now U.S. Pat. No. 4,544,953 issued on Oct. 1, 1985, for David A. Goldman and assigned to the assignee herein.

Thus such techniques for providing a signal for the focus motor 96 are known in the art and, essentially as one can see from FIG. 2, as the motor 96 is controlled to operate, the lens assembly 52 will be moved farther or closer to the lens assembly 53 to thereby provide optimum focussing. Thus the system operates to provide a magnified image whereby the magnification factor is a function of the magnification of the microscope eyeglass assembly worn by the surgeon and whereby the lens assembly is further controlled so that the image, as presented to the video monitor, is constantly and continuously focussed during the entire procedure.

It is, again, interesting to note that the scheme of automatic focussing as indicated in the above noted co-pending application utilizes the television signal and operates to analyze the high frequency content of the signal to provide focussing for the optical system.

Thus the above described system enables a viewer to perceive the entire operating procedure exactly as perceived by the surgeon and to present a magnified image at the same magnification as used by the surgeon for presentation to a video display or other device. The system provides operating area illumination while, because of the head-mounting arrangement, enables the surgeon to aim the headlight and, in doing so, assuring that the recorded image is that image which the surgeon actually perceives.

I claim:

1. A head-mounted coaxial imaging system of the type adapted to be supported on the head of the user by means of a headband worn by the user comprising:
   a tiltable reflecting surface mounted on said headband and positioned above the eyes of said user when said headband is being worn,
   a housing coupled to said headband and positioned above the head of said user said housing having an internal hollow and a front portion extending from said headband and overlying said reflecting surface, light means associated with said housing to project a beam of light with said beam directed to the surface of said reflecting surface whereby said beam as reflected is directed toward an area of observation,
   an adjustable magnification means located in the hollow of said housing and operative to receive an image of said area of observation as reflected by said tiltable reflecting surface for magnifying said image of said area according to the preferences of said user and means optically coupled to said magnification means for producing a viewable image of said area of observation.

2. The head-mounted coaxial imaging system according to claim 1 wherein said tiltable reflecting surface includes a planar mirror member pivotally mounted to a depending bracket coupled to said front portion of said headband.

3. The head mounted coaxial imaging system according to claim 2, wherein said mirror is tilted with respect to said housing to provide an optical path which is substantially coaxial to the apth of the eyes of said user.

4. The head-mounted coaxial imaging system according to claim 1, wherein said lighting means includes a fiber optic cable mounted on said housing and capable of propagating a beam of light into said front portion of said housing and means for directing said beam of light from said front portion of said housing to said tiltable reflecting surface.

5. The head-mounted coaxial imaging system according to claim 4 wherein said means for directing said beam of light comprises a first surface mirror mounted on said front portion of said housing and directed at an angle sufficient to direct said beam onto said tiltable reflecting surface.

6. The head-mounted coaxial imaging system according to claim 1, further including reflecting means mounted in said front portion of said housing positioned to intercept said image as reflected from said tiltable reflecting surface indicative of said area of observation and to direct said reflected image into said housing.

7. The head-mounted coaxial imaging system according to claim 6, wherein said adjustable magnification system is positioned to receive said reflected image for magnifying the same according to the preference of said viewer.

8. The head-mounted coaxial imaging system according to claim 7, wherein said adjustable magnification system includes a first input lens assembly for receiving said reflected image, a second output lens assembly responsive to said reflected image and a central magnification lens assembly positioned between said input and output lens assembly and responsive to said reflected image to magnify the same.

9. The head-mounted coaxial imaging system according to claim 8, wherein said lens assemblies are movably mounted in said housing to enable a change in distance between said lenses and therefore a change in magnification and focussing.

10. The head-mounted coaxial imaging system according to claim 9, further including selector means coupled to said lens assemblies for moving said assemblies with respect to one another for changing the magnification of said magnification means.

11. The head-mounted coaxial imaging system according to claim 9, further including automatic focussing means coupled to said lens assemblies for moving said assemblies with respect to one another for varying the focus of said magnification system.

12. The head-mounted coaxial imaging system according to claim 1, wherein said means optically coupled to said magnification system includes a television camera.

13. The head-mounted coaxial imaging system according to claim 1 wherein said user further views said area of observation through a microscope eyeglass assembly for imparting a given magnification, means for selecting the magnification of said area of observation according to said given magnification.

14. A head mounted coaxial imaging system of the type to be supported on the head of a user by means of a headband worn by the user, said user further wearing a microscope eyeglass assembly for enabling said user to view an area of observation with a given magnification due to said eyeglass assembly comprising in combination, a reflector surface depending from the front of said headband and positioned above the eyes of said user, said reflector surface positioned at given angle to project a beam of light towards an observation area viewed by said user, a hollow housing coupled to said headband and positioned above the head of said user, said housing having an output port positioned above said reflector surface and capable of optically communicating with said surface, light propagating means located on said housing and operative to direct a beam of light through said output port on said reflector surface to be directed to said observation area as determined by the movement of the head of said user, a variable magnification lens assembly means located within the hollow of said housing and having an aligned optical axis, said lens assembly including reflecting means responsive to the image of said observation area as reflected by said reflector surface for directing said image along said aligned optical path for causing said magnification lens assembly to magnify said image according to the magnification provided by said microscope eyeglass assembly and means coupled to said variable magnification lens assembly to provide a display of said observation area as substantially viewed by said user with said given magnification.

15. The head-mounted coaxial imaging system according to claim 14, wherein said reflector surface is pivotally mounted with respect to said headband to enable the selective tilting of said reflector surface with respect to said area of observation whereby said reflector surface can be tilted to accommodate a given working distance according to the vision of said user.

16. The head-mounted coaxial imaging system according to claim 14, wherein said light propagating means includes a fiber optical cable mounted on said housing for propagating a beam of light and means for reflecting said beam of light onto the surface of said reflecting surface wherein said means includes a condensor lens assembly and a first surface mirror with said mirror mounted on the surface of said housing at a given angle.

17. The head-mounted coaxial imaging system according to claim 14, further including selector means coupled to said variable magnification system for selecting said magnification according to the magnification afforded by said microscope eyeglass assembly.

18. The head-mounted coaxial imaging system according to claim 14, wherein said means coupled to said variable magnification system includes a television camera.

19. The head-mounted coaxial imaging system according to claim 14, further including automatic focussing means coupled to said variable magnification means for controlling the focussing of said means.

20. The head-mounted coaxial imaging system according to claim 14, wherein said adjustable magnification means includes an input lens assembly for receiving said reflected image, an output lens assembly for propagating said reflected image and a magnification lens assembly positioned between said input and output assemblies for magnifying said reflected image.

* * * * *